United States Patent [19]

Garner et al.

[11] Patent Number: 4,685,966

[45] Date of Patent: Aug. 11, 1987

[54] SURFACE TRACKING APPARATUS

[75] Inventors: Gerald D. Garner; Walter E. Wozniak, both of Florissant, Mo.

[73] Assignee: McDonnell Douglas Corporation, Long Beach, Calif.

[21] Appl. No.: 760,265

[22] Filed: Jul. 29, 1985

[51] Int. Cl.$^4$ ............................................. G01N 29/04
[52] U.S. Cl. ..................................... 73/583; 73/618; 73/619; 73/634
[58] Field of Search ................. 73/583, 618, 619, 633, 73/634, 640, 105; 901/14

[56] References Cited

U.S. PATENT DOCUMENTS

| | | | |
|---|---|---|---|
| 773,983 | 11/1904 | Reisner | 73/105 |
| 2,363,691 | 11/1944 | Reason | 73/105 |
| 2,474,015 | 6/1949 | Shaw | 73/105 |
| 3,043,448 | 7/1962 | Melton | 901/14 |
| 3,056,209 | 10/1962 | Oliver | 73/105 |
| 3,329,011 | 7/1967 | Dereng | 73/105 |
| 3,470,739 | 10/1969 | Takafuji et al. | 73/105 |
| 4,418,698 | 12/1983 | Dory | 73/633 |
| 4,555,217 | 11/1985 | Wright | 901/14 |
| 4,581,938 | 4/1986 | Wentzell | 73/634 |

FOREIGN PATENT DOCUMENTS 2734042 3/1978 Fed. Rep. of Germany ........ 73/634

*Primary Examiner*—Anthony V. Ciarlante

*Attorney, Agent, or Firm*—James M. Skorich; George W. Finch; John P. Scholl

[57] ABSTRACT

Apparatus for continuously orienting an ultrasonic transducer so that the emitted ultrasonic waves remain at a normal angle of incidence to the opposing surface of an object while the transducer is being moved laterally across the surface in order to inspect the subsurface composition of the object. The sensor casing which contains the ultrasonic transducer pivots about one end of a tubular support arm, while the other end of the support arm pivots about a gearbox casing. A drive shaft passes through the support arm and has a miter gear on each end. One miter gear is engaged with a miter gear attached to the gearbox casing, and the other is engaged with a miter gear attached to the sensor casing so that the rotation of the drive shaft causes the simultaneous rotation of the support arm about the gearbox casing and, in the opposite direction, the rotation of the sensor casing about the support arm. The gearbox casing is attached to a carriage and has the freedom to roll relative to it. The carriage is a part of a translational motion apparatus which continuously moves the sensor casing across the surface of the object. The gear ratios are calculated so that, in conjunction with rolling the apparatus, a normal angle of incidence between the emitted ultrasonic waves and the surface of the object can be obtained regardless of the local orientation of the surface.

17 Claims, 7 Drawing Figures

SURFACE TRACKING APPARATUS

BRIEF DESCRIPTION OF THE PRIOR ART AND SUMMARY OF THE INVENTION

This invention pertains to tracking the surface area of an object and, more particularly, to tracking the surface area with a transducer emitting ultrasonic waves which are kept at a normal angle of incidence to the surface.

The current generation of supersonic high performance aircraft have many parts, such as the wings and horizontal stabilizers, which are comprised of laminated layers. Parts constructed of this composite are lighter and easier to manufacture (especially where the part includes compound curves) than metal parts having comparable parameters. Due to the manner of their manufacture, however, these laminated parts are particularly susceptible to bonding flaws which cannot be detected by visual inspection. Such defects eventually lead to structural failure and, given the aeronautical use of the part, the consequences can be catastrophic.

The manufacturers of such laminated aircraft parts have used X-rays in attempting to detect defects in the parts. However, X-ray film is expensive, and determining the appropriate power setting on the X-ray machine can be difficult and time consuming. In addition, X-rays cannot detect the difference in density between the laminated composite and air, a significant problem because separation in the layers of laminate occasioned by defective bonding will typically be evinced by an air pocket.

Ultrasonic waves have also been employed to nondestructively test laminated parts, and their use has been found preferable to that of x-rays because they are able to detect the difference in density between the laminate composite and air, as well as being easier and faster to use, and costing less. There are presently two systems which use ultrasonic waves to nondestructively test a part, through transmission and pulse echo. Through transmission apparatus sends ultrasonic waves through the aircraft part to a receiver located opposite the sending unit on the other side of the part, and inspects the material by measuring the attenuation of the waves caused by their passage through the part. More particularly, delamination or the presence of a foreign body in the subsurface structure will cause an ultrasonic wave to attenuate more than would be the case when no subsurface anomaly is present.

Pulse echo apparatus sends the ultrasonic waves into the part with the same transducer which subsequently receives the reflected echoes. A first echo is reflected from the opposing, or first, surface of the part, and a second, weaker echo is obtained by the ultrasonic wave continuing through the thickness of the part and reflecting off of the back, or second, surface. However, the presence of a foreign object or flaw in the subsurface structure will also cause the second echo. The existence of a subsurface anomaly is discovered by comparing the interval between the first and second echoes with a normal interval caused by the second echo reflecting off of the back surface, with a shorter than normal interval being indicative of a subsurface irregularity.

Common to both the through transmission and pulse echo systems is the requirement that the angle of incidence between the ultrasonic waves and the surface of the part be very close to normal, with pulse echo having a much tighter tolerance than through transmission.

With regard to the through transmission apparatus, the respective transducers for sending and receiving the ultrasonic waves are mounted on individual carriages located on opposite sides of the object to be inspected. The carriages are carried, respectively, by tubes which descend vertically from two subcarriages, and the height of the carriages is controlled by motors located in the subcarriages. The carriages both travel on a common bridge situated above the object and transverse to the longitudinal axis of the object. Linear movement of the subcarriages along the bridge provides for lateral motion of the transducers, and common longitudinal translation of the carriages is obtained by the movement of the entire bridge along rails situated parallel to the longitudinal axis of the object.

The mechanical apparatus used to provide translational motion for the sole transducer employed in the pulse echo system is the same as that described for the through transmission transducers, except that only one subcarriage and carriage assembly is used instead of two.

When two carriage-subcarriage assemblies are used to translate through transmission apparatus, the two assemblies move laterally along the bridge in order to keep the proper distance between the respective transducers and the object, while the inspection of the object along a horizontal line is obtained by the longitudinal movement of the entire bridge. When the edge of the object is reached, the carriages are moved downward (or upward, if desired) a predetermined amount by the vertical tubes, and this horizontal line is then scanned in the manner previously described. This procedure is repeated until the entire area is inspected.

Due to the requirement that the angle of incidence between the ultrasonic waves and the surface of the object be approximately normal, the process must be interrupted and the part physically rotated whenever the angle of incidence deviates from normality in excess of the maximum tolerance. With the shape of laminate composite parts becoming more complex, it has become increasingly difficult to maintain the required angular alignment, with the result that the time, and therefore the cost, necessary to examine a part has considerably increased.

One attempt at overcoming the problem of maintaining normal incidence has been to allow the transducer to rotate in a vertical plane about a horizontal axis that passes through its carriage and lies parallel to the longitudinal axis of the object. The problem with this solution lies in the difference between the location of the target point of incidence of the ultrasonic waves emitted from a fixed or unrotated transducer and the point of incidence of the ultrasonic waves when the transducer is rotated. The apparatus of the prior art attempts to reduce this error by vertically moving the transducer carriage, but even with this modification the apparatus can only provide normal incidence when the object's surface lies very close to parallel with the longitudinal axis of the object.

Even if the transducer was provided with an additional degree of rotational freedom about a vertical axis, the receiving transducer of a through transmission apparatus would have to be longitudinally moved relative to the sending transducer in order to remain linearly aligned with it. As the sending and receiving transducers are mounted on carriages suspended from subcarriages which travel on a common transverse bridge, the location error introduced by transducer rotation about a vertical axis could not be corrected because independent longitudinal motion of the carriages relative to each other is not possible.

Where a pulse echo transducer is used, longitudinal carriage movement to correct for target location error occasioned by transducer rotation about a vertical axis would be possible. However, a surface having a local compound curvature, that is, a surface locally comprised of several radii of curvature that are not co-planar, requires more than one degree of rotational freedom of the transducer in order, to obtain normal incidence. In addition to requiring cooperation between the several degrees of freedom, the movement of the carriage would have to be modified so that it would eliminate the target location error as well as continuously moving along the appropriate horizontal track, and this would require modification of the successful computer program currently used to control the movement of the translational motion apparatus.

The present invention solves these problems by providing a surface tracking apparatus which keeps the ultrasonic waves emitted by the transducer normal to the surface of the object being inspected regardless of the local orientation or contour of the surface. The present invention is attached to conventional translational motion apparatus and requires no change in the computer software currently used in conjunction with such apparatus. For the through transmission mode, one surface tracking apparatus is attached to each of the carriages which are located on opposite sides of the object being inspected. When a pulse echo transducer is being used, only one carriage and attached surface tracking apparatus need be employed.

A sensor casing containing an ultrasonic transducer is rotatably attached to one end of a tubular support member, with the other end of the support member being rotatably attached to a gearbox casing. The gearbox casing is rotatably attached to a carriage, which is a part of the translational motion apparatus. The sensor casing and the support member each have a rotational degree of freedom about respective parallel axes that remain in respective planes that are parallel to the longitudinal axis of the object. A cylindrical drive shaft having a miter gear on each end passes through the center of the support member. The gear on one end of the shaft meshes with a gear attached to the gearbox casing, while the gear located on the other end of the shaft meshes with a gear attached to the sensor casing. The gears attached to the gearbox casing and the sensor casing are situated on opposite sides of the drive shaft so that rotation of the drive shaft causes rotation of the support member about the gearbox casing, while simultaneously causing the rotation of the sensor casing relative to the support member in a direction opposite that of the support member relative to the gearbox casing. The length of the support member (more precisely, the distance between the rotational axis of the support member about the gearbox casing and the rotational axis of the sensor casing), the distance between the rotational axis of the support member about the gearbox casing and the surface of the object being tested, and the gear ratios are selected so that the point of incidence of the ultrasonic waves with the surface of the object remains virtually unchanged regardless of the joint rotation of the support member and the sensor casing.

The gearbox casing is rotatably attached to the carriage in a manner that allows it the freedom to roll about an axis lying transverse to the longitudinal axis of the object. The joint rotation of the support member and the sensor casing in combination with the rolling of the gearbox casing allows the surface tracking apparatus to obtain an approximately normal angle of incidence for the emitted ultrasonic waves for any orientation of the opposing surface of the object.

The joint rotation of the support member and the sensor casing and the roll of the gearbox casing is obtained by motors governed by an appropriately programmed microcomputer. Data numerically describing the contour of the surface of the object to be inspected is input into the microcomputer prior to the inspection. During the tracking of successive horizontal lines across the object's surface by the surface tracking apparatus, the microcomputer rapidly rotates the support member and the sensor casing and rolls the gearbox casing to obtain normal incidence for the emitted ultrasonic waves upon each of a sequence of points located along each of the tracked horizontal lines. The collected test data is transformed into digital form and can be either plotted on paper or displayed on a video monitor.

The present invention eliminates the incessant interruptions previously necessary to physically rotate the part to obtain normal incidence for the emitted ultrasonic waves. In addition, it avoids the delay, high costs and other problems attendant to inspecting aircraft parts with x-rays. The invention is a simple addition to the conventional translational motion apparatus and its attendant computer hardware and software for both the through transmission and pulse echo modes of operation, and can be attached without requiring their modification

DETAILED DESCRIPTION OF THE DRAWINGS

Figure 1:
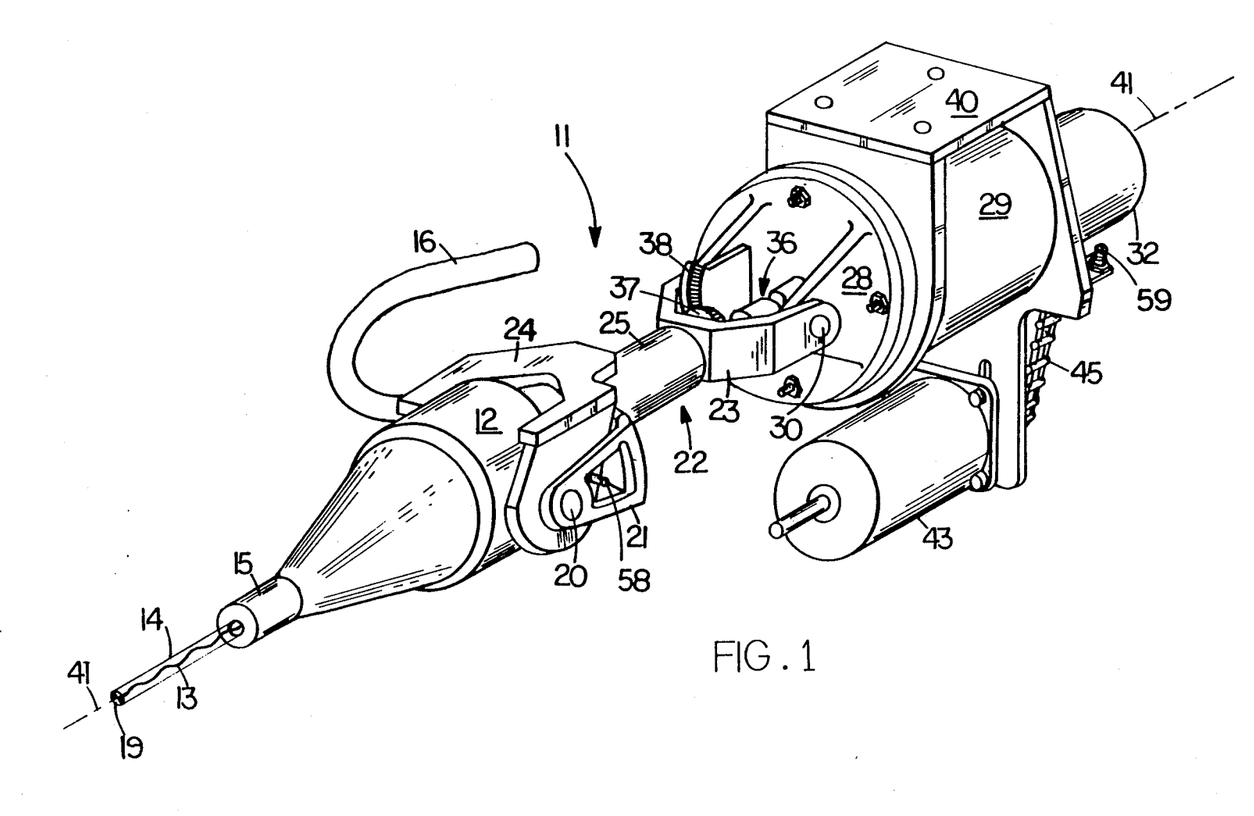
FIG. 1 is a perspective view of the preferred embodiment of the present invention.
Figure 2:
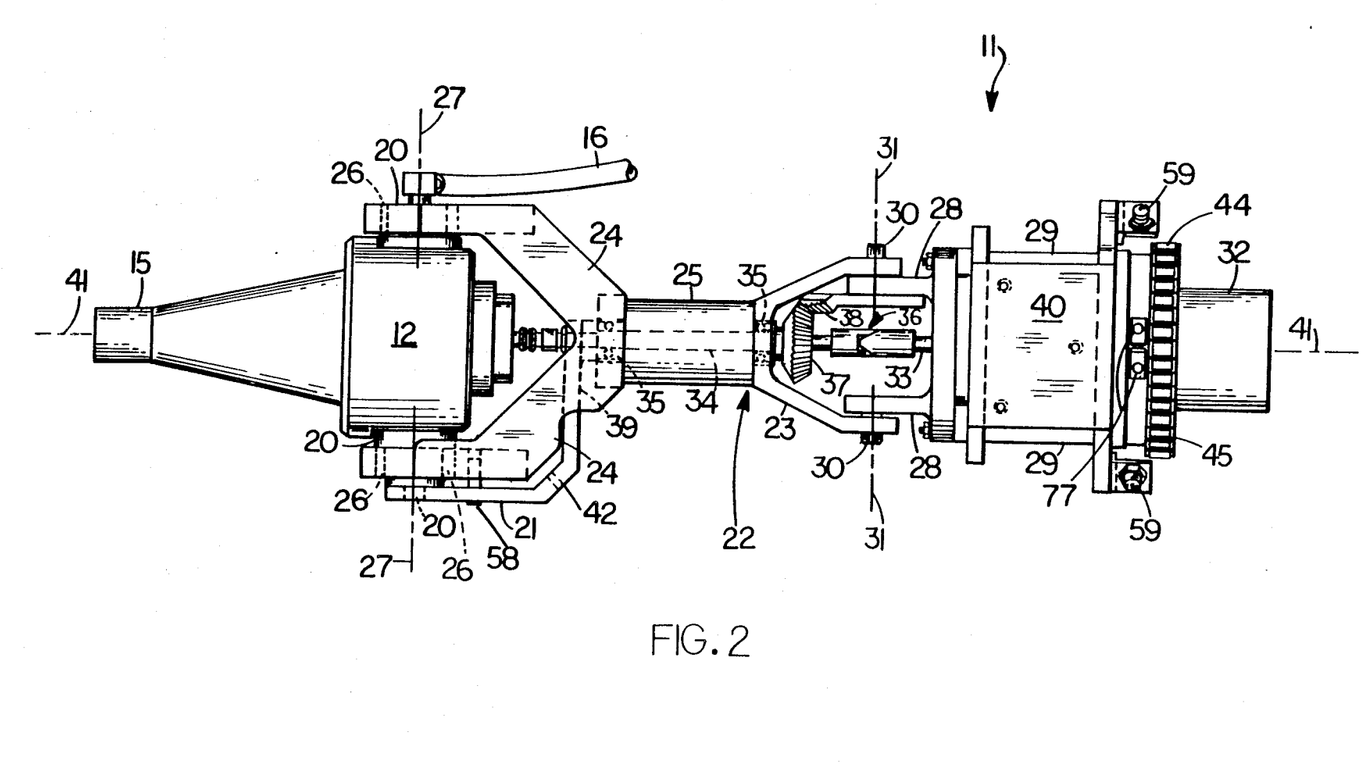
FIG. 2 shows a top view of the preferred embodiment of the present invention.
Figure 3:
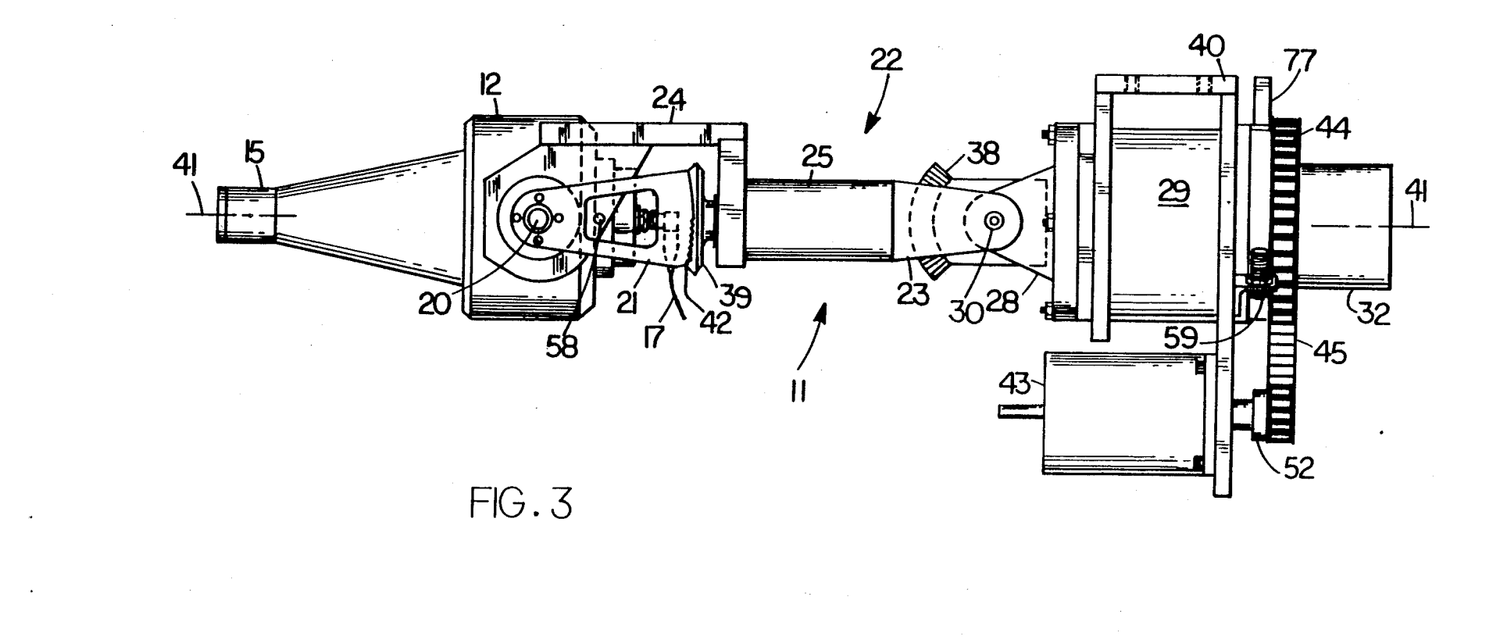
FIG. 3 is a side view of the preferred embodiment of the present invention.

Reference is now made to the drawings, particularly FIGS. 1, 2 and 3, which illustrate surface tracking apparatus 11, a preferred embodiment of the present invention. A sending transducer which emits ultrasonic waves is housed in sensor casing 12. The sending transducer emits ultrasonic waves 13 and cylindrical stream of water 14 from sensor casing nozzle 15 such that ultrasonic waves 13 travel within stream of water 14. Hose 16 transports water between a source (not shown) and sensor casing 12. Wiring 17 electrically connects the sending transducer with the other electrical components of surface tracking apparatus 11.

Aircraft part 18 (shown in FIG. 5) is located opposite sensor casing 12 of surface tracking apparatus 11. Target 19 is located on the surface of part 18, and is at the point of incidence of ultrasonic waves 13 and stream of water 14. Sensor casing 12 is fixedly attached to trunnion 20. Miter gear 21 is fixedly attached to one end of trunnion 20. Support member 22 is comprised of base end 23, cantilever end 24, and hollow cylindrical section 25. Hollow cylindrical section 25 lies in between and connects base end 23 and cantilever end 24. Trunnion 20 is rotatably situated in bearings 26, while bearings 26 rest in circular openings in cantilever end 24, thereby allowing sensor casing 12 and miter gear 21 to rotate about lateral axis 27.

Parallel brackets 28 extend from gearbox casing 29. Base end 23 is rotatably connected to brackets 28 by rotational joints 30. Rotational joints 30 allow support member 22 to rotate about major lateral axis 31, an axis that is parallel to lateral axis 27. Pitch motor 32 is attached to gearbox casing 29. Gearbox casing 29 is cylindrical and contains a gearbox which reduces the output from pitch motor 32. Gearbox output shaft 33 extends from gearbox casing 29 and is driven by pitch motor 32. Drive shaft 34 lies within hollow cylindrical section 25 and is free to rotate therein about its longitudinal axis because it is rotatably supported at both ends of cylindrical section 25 by annular ball bearings 35. One end of drive shaft 34 is rotatably connected to gearbox output shaft 33 along major lateral axis 31 by means of universal joint 36.

Miter gear 37 is annularly attached about drive shaft 34 near the end of drive shaft 34 which is rotatably attached to gearbox output shaft 33. Miter gear 38 is fixedly attached to one of brackets 28, and is engaged with miter gear 37. The other end of drive shaft 34 protrudes from the end of hollow cylindrical section 25 and has miter gear 39 fixedly attached about its circumference, with miter gear 39 being engaged with miter gear 21 along gear interface 42. Stop 58 is attached to cantilever 24, and serves to limit the rotation of miter gear 21 and trunnion 20.

Miter gear 38 and miter gear 21 are mounted on opposite lateral sides of support member 22. The actuation of pitch motor 32 causes the rotation of gearbox output shaft 33, which, in turn, causes the rotation of drive shaft 34. Since drive shaft 34 is contained within hollow cylindrical section 25, the rotation of miter gear 37 relative to miter gear 38 causes the rotation of drive shaft 34 about major lateral axis 31 and, therefore, support member 22 about rotational joints 30 and major lateral axis 31. The rotation of drive shaft 34 about its longitudinal axis also causes miter gear 39 to rotate miter gear 21, resulting in the rotation of trunnion 20 and sensor casing 12 about lateral axis 27 in a direction opposite that of support member 22 about major lateral axis 31.

The gear ratios, the distance between lateral axis 27 and major lateral axis 31, and the distance between major lateral axis 31 and target 19 are dependent variables which can be calculated by methods known to those skilled in this particular art so that ultrasonic waves 13 will remain incident upon target 19 regardless of the angle of rotation of support arm 22 about rotational joints 30 (and major lateral axis 31) and the concomitant rotation of sensor casing 12 about lateral axis 27.

Gearbox casing 29 is situated in two circular openings in carriage 40 in a manner that allows it the freedom to rotate about longitudinal axis 41, but prevents it from translationally moving with respect to carriage 40. Roll motor 43 is mounted on carriage 40. Drive sprocket 52 is connected to and driven by roll motor 43. Sprocket 44 is attached to gearbox casing 29 with its axis of rotation coinciding with longitudinal axis 41. Sprocket chain 45 is a closed loop, and is engaged with sprocket 44 and drive sprocket 52. The actuation of roll motor 43 causes the rotation of drive sprocket 52, forcing sprocket chain 45 to rotate sprocket 44, and thereby causing the rotation of pitch motor 32, gearbox casing 29, support member 22 and sensor housing 12 about longitudinal axis 41.

Roll limit switches 59 are attached to carriage 40. Limit switch trip 77 is attached to gearbox casing 29. Contact between limit switch trip 77 and either of roll limit switches 59 shuts off roll motor 43, and functions to prevent excessive roll of surface tracking apparatus 11 that would result in hose 16 and wiring 17 becoming wrapped around rotatable parts of surface tracking apparatus 11 and thereby prevent apparatus 11 from assuming a commanded pitch position or cause the rupture of hose 16 or wiring 17.

Figure 4:
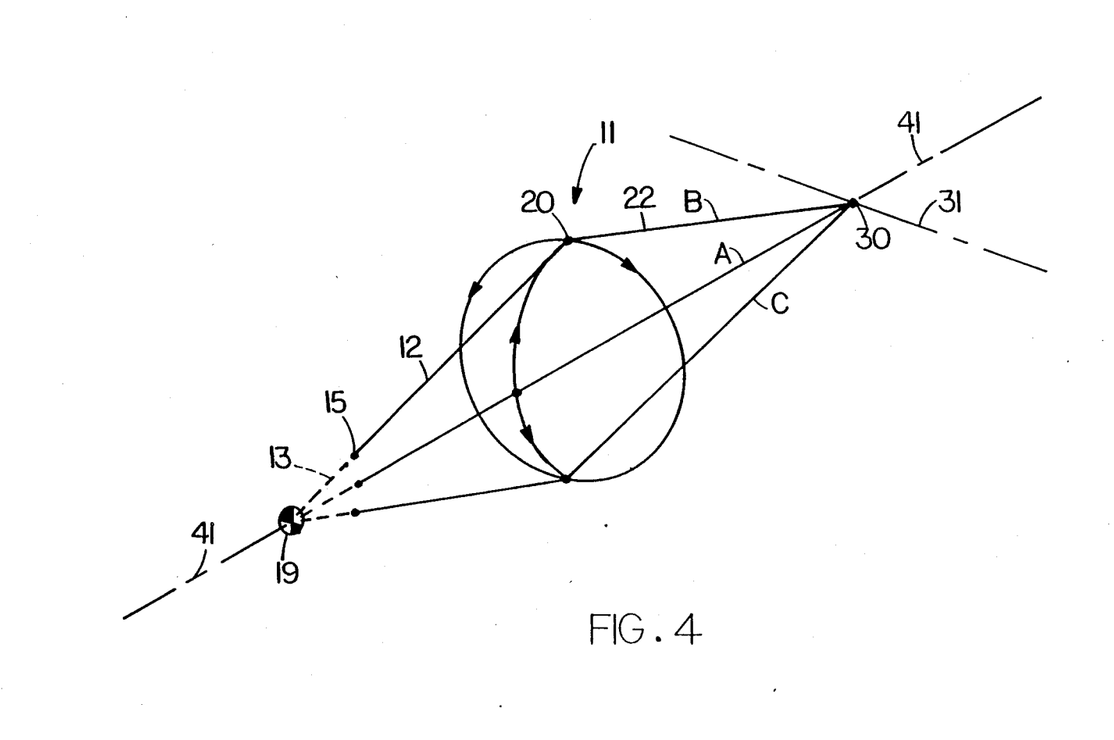
FIG. 4 is a schematic drawing of the preferred embodiment of the present invention showing it in several pitch and roll positions.

Turning to FIG. 4, surface tracking apparatus 11 is drawn schematically in several operative positions, together with target 19. In position A, support member 22 and sensor casing 12 are coincidental with longitudinal axis 41, which intersects target 19. (This is also the position of support member 22 and sensor casing 12 shown in FIGS. 1, 2 and 3.)

Positions B and C show two different angles of rotation, also known as pitch angles, for support member 22 and sensor casing 12 about major lateral axis 31 and lateral axis 27, respectively. Alternatively, position C can also be obtained by first pitching support member 22 and sensor casing 12 upwards to position B and then rolling apparatus 11 180° about longitudinal axis 41. As previously noted, although the pitch angle may change, ultrasonic waves 13 remain incident upon target 19 for all illustrated positions, as they would for any other pitch position as well as any intermediate roll position between positions B and C.

By combining pitch and roll, apparatus 11 orients sensor casing 12 to direct emitted ultrasonic waves 13 at an approximately normal angle of incidence to target 19 regardless of the local surface contour of aircraft part 18. The precise combination of pitch and roll necessary to obtain approximately normal incidence of ultrasonic waves 13 is obtained by commands to pitch motor 32 and roll motor 43, respectively, from an appropriately programmed microcomputer.

However, as the pitch angle increases, the angle of incidence of ultrasonic waves 13 upon target 19 will proportionally deviate from true normality, although even at a relatively high pitch angle the angle of incidence does not exceed the relatively tight tolerance of 2° from normality required for pulse echo testing (in comparison to a tolerance of 10° for through transmission testing). If desired, even this slight deviation from normal incidence can be eliminated by substituting eccentric gears for miter gears 21 and 39, and 37 and 38. The configuration of the eccentric gears can be determined by one skilled in the art.

As through transmission testing detects a flaw by measuring the attenuation of an ultrasonic wave that passes through the object being inspected, it requires a sending transducer on one side of the object and a receiving transducer on the other. The angle of incidence of the ultrasonic waves emitted by the sending transducer must be within 10° of normality to the surface of the target. The receiving transducer must be linearly aligned with the sending transducer. The angle between the receiving transducer and the surface of the part facing the receiving transducer is not critical.

Figure 5:
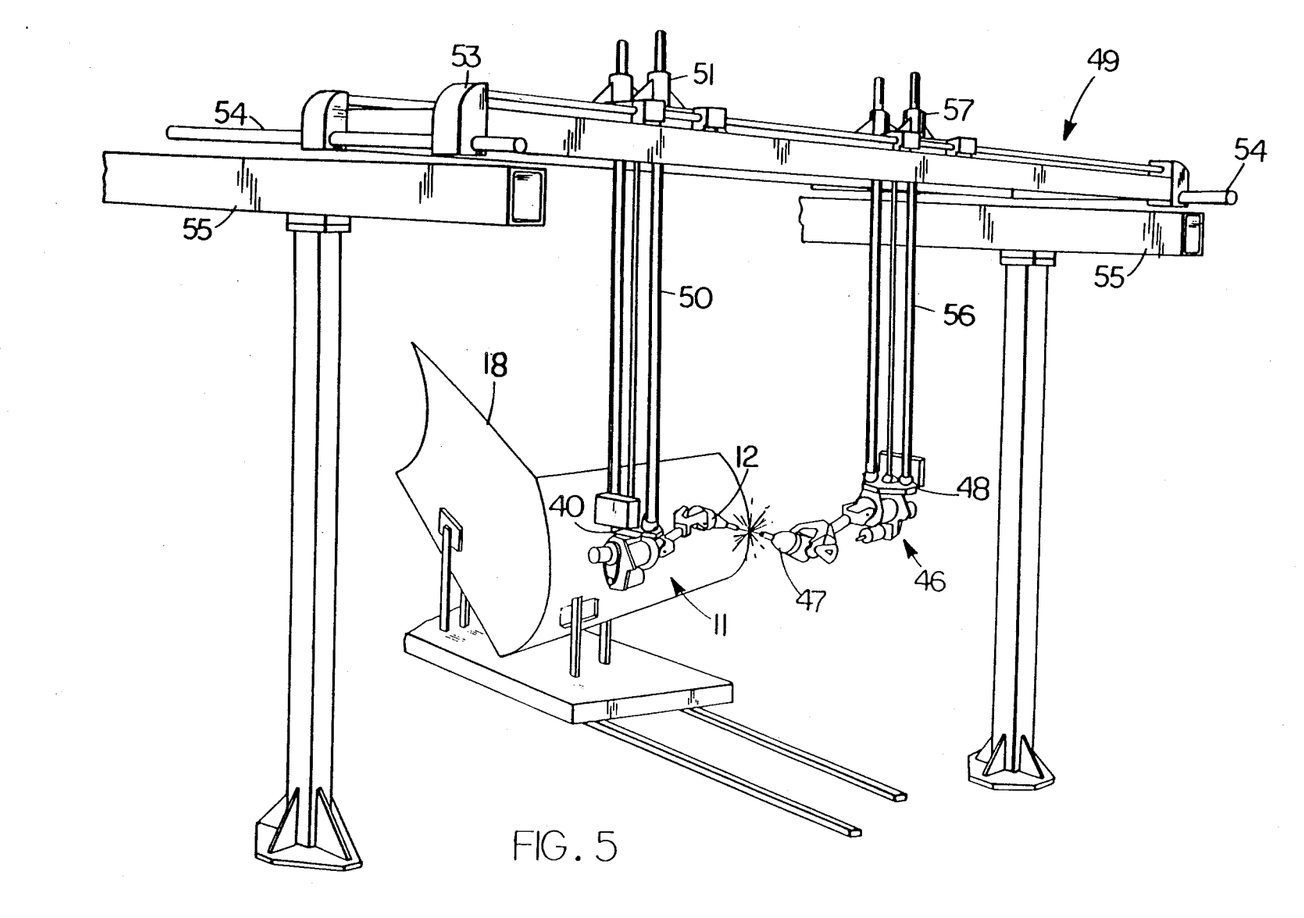
FIG. 5 is a perspective drawing of the preferred embodiment of the present invention shown mounted on a translational motion apparatus and being operatively employed to inspect an aircraft part.

Thus, as shown in FIG. 5, two of the surface tracking apparatus of the present invention are employed to inspect aircraft part 18 using the through transmission test mode. One apparatus is surface tracking apparatus 11, which includes a sending transducer contained in sensor casing 12. The sending transducer is electrically connected to and excited by a pulser (as will be further discussed in conjunction with FIG. 6). The other apparatus, surface tracking apparatus 46, is identical to surface tracking apparatus 11. However, although the transducer contained in sensor casing 47 is identical to that contained in sensor casing 12, it is electrically connected to an amplifier and functions to receive the attenuated ultrasonic waves 13.

Surface tracking apparatus 46 is attached to carriage 48, and both carriage 40 and carriage 48 are attached to translational motion apparatus 49. More particularly, carriage 40 is attached to vertical tubes 50. Tubes 50 are suspended from and move vertically through subcarriage 51. Subcarriage 51 moves laterally with respect to part 18 along bridge 53. Bridge 53 lies transverse to the longitudinal axis of part 18, and is suspended above and moves longitudinally with respect to part 18 along parallel rails 54. Rails 54 are structurally supported by box beams 55 (the actual attachments at the ends of rails 54 are not shown).

Carriage 48 is attached to vertical tubes 56. Tubes 56 are suspended from and move vertically through subcarriage 57. Subcarriage 57 moves laterally with respect to aircraft part 18 along bridge 53.

The translational motion of carriages 40 and 48 (and thus surface tracking apparatus 11 and 46) is obtained by a combination of the vertical movement of tubes 50 and 56 through subcarriages 51 and 57, respectively; the lateral movement of subcarriages 51 and 57 along bridge 53; and the longitudinal movement of bridge 53 along rails 54. The movement of these three parts is obtained by respectively connected motors (not shown). The translational motion of carriages 40 and 48 is controlled by a microcomputer instructed by a program known in the art. Carriage 40 travels longitudinally and horizontally at a lateral distance from the surface of aircraft part 18 that approximates the focal length of the sending transducer contained in sensor casing 12 so that ultrasonic waves 13 impinge upon part 18 near their maximum power density.

Bridge 53 carries both subcarriages 51 and 53. Thus carriage 48 moves longitudinally along with carriage 40. The microcomputer controls the vertical movement of carriages 40 and 48 so that they remain at the same height as well. In operation, carriage 40 is moved longitudinally so that longitudinal axis 41 tracks a horizontal line on the opposing surface of aircraft part 18. Upon reaching the end of aircraft part 18, the longitudinal motion of carriage 40 is stopped and carriage 40 is moved downward (or upward) an incremental distance, after which its longitudinal motion is resumed in the opposite direction along this lower (or upper) horizontal line. The foregoing procedure is repeated until all of the opposing surface of part 18 is covered.

Before the inspection, data describing the contour of aircraft part 18 facing surface tracking apparatus 11 is compiled. One means to accomplish this is to mount a mapping apparatus identical to surface tracking apparatus 11 on carriage 40 adjacent to apparatus 11 with the longitudinal axis of the mapping apparatus situated in parallel with longitudinal axis 41. The transducer housed in the sensor casing of the mapping apparatus operates in the pulse echo mode and emits ultrasonic waves in the direction of the opposing aircraft part 18. The mapping apparatus does not pitch and roll along with surface tracking apparatus 11, however, but remains colinear with its own longitudinal axis (as illustrated by position A in FIG. 4). The distance between the mapping transducer and the opposing point on the surface of aircraft part 18 is computed from the time taken for the return of the first echo of each emitted ultrasonic wave. This distance parameter is used in conjunction with the continuously monitored longitudinal and vertical coordinates of each point to obtain a topographical grid. A suface contour map is then derived by interpolating between each point of the grid, and the slope of any point on the map may then be obtained. The calculations performed to derive the slope from the raw coordinate and distance data are performed by a microcomputer employing a program obvious to one skilled in the art. Of course, the mapping apparatus must be sufficiently offset from surface tracking apparatus 11 to allow the contour map to be developed prior to the testing of any point within its boundaries.

During the horizontal translational movement of carriage 40, the precise location of the intersection of longitudinal axis 41 with the opposing surface of aircraft part 18, that is, target 19, is continuously monitored. The surface contour data together with the instantaneous location of target 19 are used by an appropriately programmed microcomputer to suitably actuate pitch motor 32 and roll motor 43 to orient sensor casing 12 so that ultrasonic waves 13 remain within a desired tolerance of normal incidence to target 19.

The microcomputer governing the pitch and roll of surface tracking apparatus 11 also controls the orientation of surface tracking apparatus 46 to keep the receiving transducer contained within sensor casing 47 aligned with the sending transducer contained within sensor casing 12 so that the receiving transducer receives ultrasonic waves 13.

Figure 6:
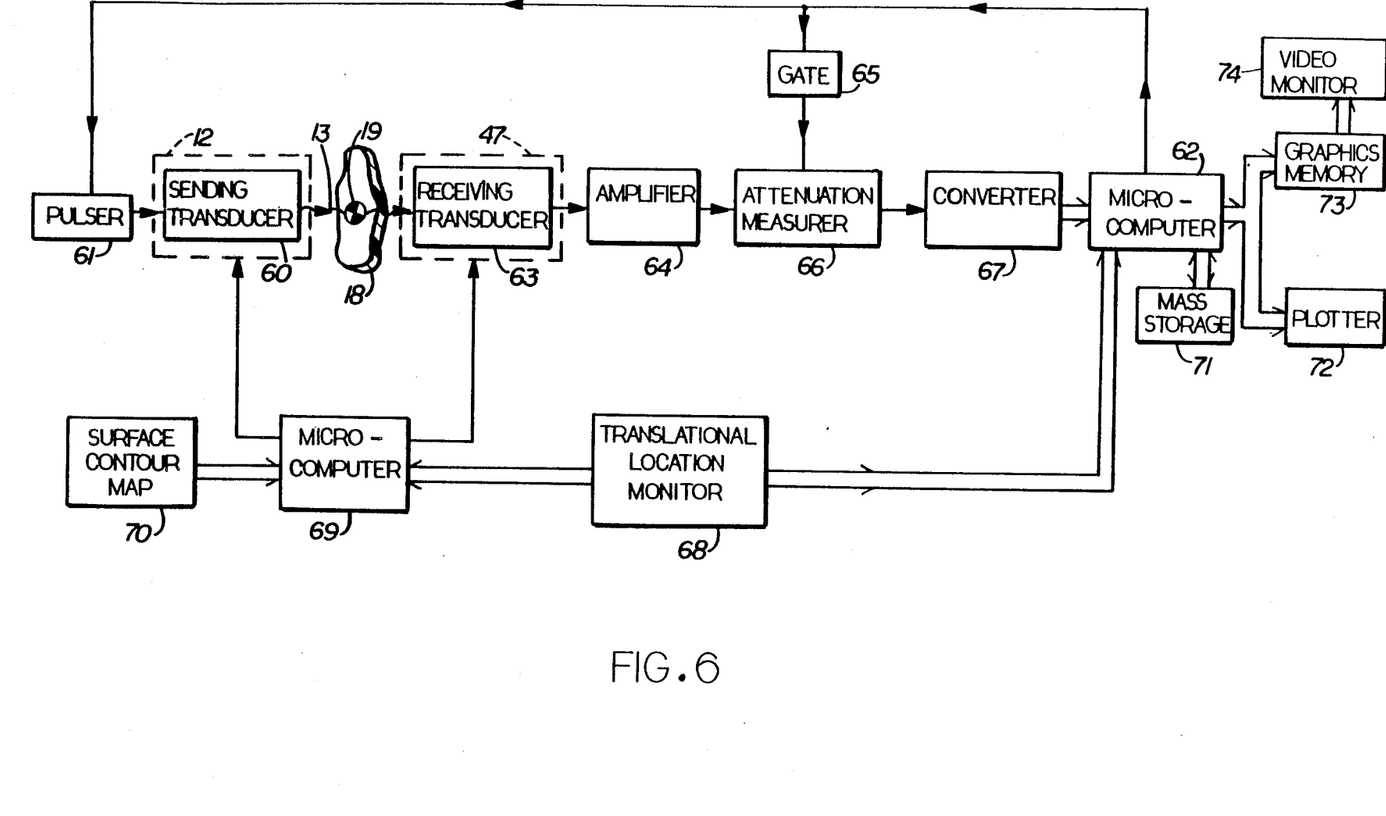
FIG. 6 is a schematic drawing of the preferred embodiment of the present invention operating in the through transmission mode, and particularly showing how the wave attenuation data is obtained, processed and collated.

FIG. 6 is a schematic drawing of surface tracking apparatus 11 and surface tracking apparatus 46 of the present invention operating in the through transmission mode. Sending transducer 60 is located in sensor casing 12. Pulser 61 produces periodic voltage pulses upon receiving periodic trigger signals from microcomputer 62. Each pulse excites sending transducer 60 and causes it to emit ultrasonic waves 13. Ultrasonic waves 13 impinge upon aircraft part 18 at target 19, continuing through the thickness of aircraft part 18 to impinge upon receiving transducer 63 located in sensor housing 47. Receiving transducer 63 transforms the acoustic energy of ultrasonic waves 13 back into electrical energy in the form of voltage pulses. The output of receiving transducer 63 is amplified by amplifier 64.

Gate 65 opens to allow attenuation measurer 66 to measure only the first (and largest) pulse caused by each of waves 13 (as modulated by amplifier 64). This function is accomplished by limiting the interval during which gate 65 is open, and by delaying the opening of gate 65 for a brief period after it receives the trigger signal emanating from microcomputer 62. The delay period is a function of the distance between sending transducer 60 and receiving transducer 63, and the speed of sound through water and aircraft part 18.

Attenuation measurer 66 calculates the difference between the output amplitude of amplifier 64 and a constant theoretical value. This difference represents the amount of attentuation suffered by ultrasonic wave 13 in passing through aircraft part 18. Attenuation exceeding the amount than would be caused by the ordinary passage of ultrasonic wave 13 through the thickness of aircraft part 18 underlying target 19 is indicative of the presence of either a foreign object or a flaw in the laminate. The attentuation measured by attenuation measurer 66 is converted from an analog signal to a digital signal by converter 67. The digital output of converter 67 is fed into microcomputer 62.

Translation location monitor 68 continuously monitors the location coordinates of target 19 (that is, the intersection of longitudinal axis 41 with the opposing surface of aircraft part 18) as translational motion apparatus 49 moves surface tracking apparatus 11 across the surface of aircraft part 18. Microcomputer 69 is continuously informed of the location coordinates and spatial orientation of the surface of target 19 by translational location monitor 68 and surface contour map 70, respectively. Microcomputer 69 is programmed to appropriately roll and pitch the rotatable components of surface tracking apparatus 11 and 46 to keep the angle of incidence for ultrasonic waves 13 upon target 19 within 10° of normal and, in addition, to keep receiving transducer 63 aligned with sending transducer 60.

Translational location monitor 68 also provides the position coordinates of target 19 to microcomputer 62. Microcomputer 62 processes the wave attenuation information derived by attenuation measurer 66 and collates the attenuation data for each wave 13 with the location coordinates for the corresponding target 19 obtained from translational location monitor 68. The collated attentuation data points are stored in mass storage 71.

Plotter 72 is connected to microcomputer 62, and can plot the collated attenuation data points on hard copy for study and analysis. Also connected to microcomputer 62 is graphics memory 73, and connected to graphics memory 73 is video monitor 74. Together, these two components can visually present the collated àttenuation data points on the screen of the video monitor 74. Microcomputer 62 assigns a pixel to each data point, and assigns a shade of grey (or a color) to each pixel that is a function of the amount of attenuation.

The present invention can also be used to provide for pulse echo testing. For such a use, only apparatus 11 and carriage 40 are necessary, in addition to rods 50, subcarriage 51, bridge 53, rails 54 and box beams 55. Furthermore, the acoustic transducer contained in sensor casing 12 of surface tracking apparatus 11 both emits ultrasonic waves 13 and receives the echoes reflected from aircraft part 18.

Figure 7:
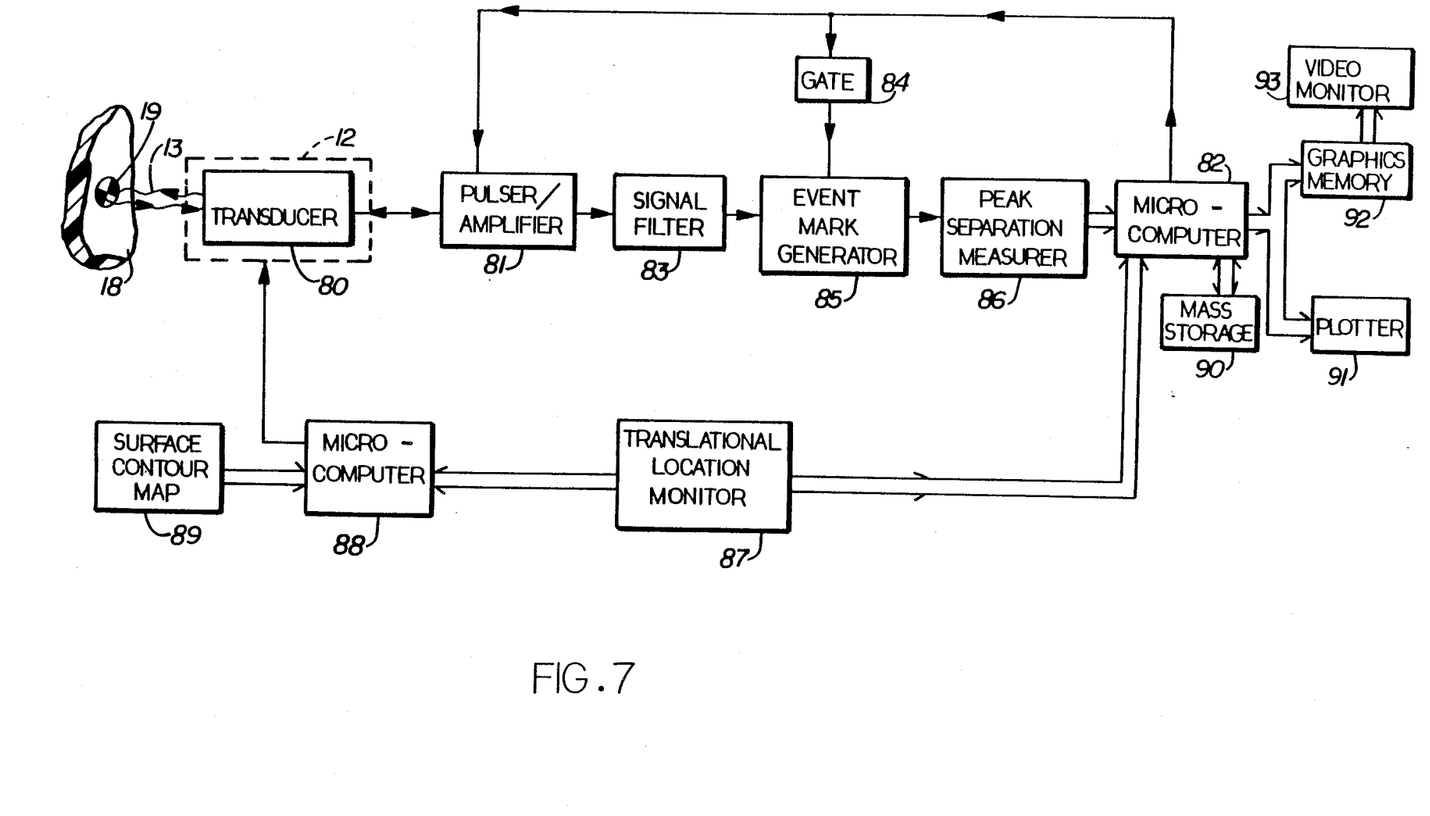
FIG. 7 is a schematic drawing of the preferred embodiment of the present invention operating in the pulse echo mode, and particularly showing how the echo interval data is obtained, processed and collated.

FIG. 7 is a schematic drawing showing surface tracking apparatus 11 of the present invention operating in the pulse echo mode. Transducer 80 is located in sensor casing 12. Pulser/amplifier 81 excites transducer 80 with periodic voltage pulses upon receiving periodic trigger signals from microcomputer 82. Upon being excited by pulser/amplifier 80, transducer 80 emits ultrasonic waves 13. Each of ultrasonic waves 13 generates a first echo from the surface of aircraft part 18 underlying target 19, as well as a second echo at a later time from either the back surface or from a subsurface anomaly. The echos are received by transducer 80, whereupon the acoustical energy is transformed into electrical energy in the form of voltage pulses. The output from transducer 80 is amplified by pulser/amplifier 81, and subsequently filtered by signal filter 83.

Gate 84 opens to allow event mark generator 85 to generate a digital event along a time scale for each of the first and second echoes from each ultrasonic wave 13 emitted by transducer 80 (as modulated by pulser/amplifier 81 and signal filter 83). This function is accomplished by delaying the opening of gate 84 for a brief period after the trigger signal emanating from microcomputer 82 is received by gate 84, with the delay period being a function of the distance between transducer 80 and target 19, and the speed of sound through water; and by having the subsequent open interval of gate 84 extend until transducer 80 emits the next ultrasonic wave 13.

Peak separation measurer 86 then measures the time separating the two event marks comprising each pair. This parameter represents the time interval occurring between the receipt by transducer 80 of the first and second echoes. A normal echo interval would be obtained from the first echo reflecting off of the opposing surface of part 18 and the second echo being created from wave 13 passing through the entire thickness of part 18 underlying target 19 and reflecting off of the back surface. A shorter echo interval is indicative of the second echo being reflected from a foreign object or a flaw in the laminate, with the precise length of the abnormally short interval providing the depth of the anomaly beneath the surface.

The output of peak separation measurer 86 is digital in form, and is fed into microcomputer 82. Translation location monitor 87 continuously monitors the location coordinates of target 19 as translational motion apparatus 49 moves surface tracking apparatus 11 across the surface of aircraft part 18. Microcomputer 88 is continuously informed of the location coordinates and spatial orientation of the surface of target 19 by translational location monitor 87 and surface contour map 89, respectively. Microcomputer 88 is programmed to appropriately pitch and roll the rotatable components of surface tracking apparatus 11 to keep the angle of incidence for ultrasonic waves 13 upon target 19 within 2° of normal.

Translational location monitor 87 also provides the position coordinates of target 19 to microcomputer 82. Microcomputer 82 processes the echo intervals derived by peak separation measurer 86 and collates the echo interval calculated for each target 19 with the target 19 location coordinates obtained from translational location monitor 87. The collated echo interval data points are stored in mass storage 90.

Plotter 91 is connected to microcomputer 82, and can plot the echo interval data points on paper. Also connected to microcomputer 82 is graphics memory 92, and connected to graphics memory 92 is video monitor 93. Together, these two components can visually present the collated echo interval data points on the screen of video monitor 93. Microcomputer 82 assigns a pixel to each data point, and assigns a shade of grey (or a color)

to each pixel that is a function of the length of the echo interval.

Changes and modifications in the specifically described embodiments can be carried out without departing from the scope of the invention, which is intended to be limited only by the scope of the appended claims.

What is claimed is:

1. An ultrasonic testing apparatus comprising:
   sensing means which emits sensing signals when sensing;
   a first linkage having said sensing means located at one end;
   translation means for moving said first linkage relative to a test object;
   first adjusting means for adjusting said first linkage;
   means for mapping the topography of said test object; and said first adjusting means receiving topographical data from said mapping means and adjusting said first linkage so that said sensing signals impinge at a desired angle of incidence on the surface of said test object.

2. The ultrasonic testing apparatus defined in claim 1 wherein:
   said members comprising said first linkage respectively rotate about parallel lateral axes; and
   said first adjusting means includes roll means for rotating said first linkage about a longitudinal axis taht lies perpendicular to said parallel lateral axes.

3. The ultrasonic testing apparatus defined in claim 2 wherein:
   said sensing signals impinge a succession of targets on said test object in a sequential order;
   said first adjusting means includes pitch motor means for rotating said plurality of members about their respective lateral axes; and
   said translation means translationally moving said first linkage so that said longitudinal axis intersects each of said targets in said sequential order.

4. The ultrasonic testing apparatus defined in claim 3 wherein
   said sensing means produces output signals upon receiving signals similar in nature to said sensing signals;
   said angle of incidence deviates no more than 2° from normality;
   echoes from said sensing signals are reflected from said test object, including a first echo and a second echo; and
   said sensing means produces a first output signal and a second output signal upon receiving said first echo and said second echo, respectively.

5. The ultrasonic testing apparatus defined in claim 4 further comprising:
   peak separation measurement means for measuring the time interval between said first output signal and said second output signal, and for generating a corresponding time interval signal;
   collating means for collating said time interval signals with said targets to form data points; and
   dispaly means for displaying said data points; whereby
   the presence of irregularities in the subsurface structure of said test object can be detected by comparing said time inteval signals with the time interval signal that would be obtained when said first echo is obtained from said sensing signal reflecting off of the surface of said test object underlying each of said targets and said second echo is obtained from said sensing signal passing through the entire thickness of said test object underlying each of said targets, respectively, and reflecting off of the back surface of said test object.

6. The ultrasonic testing apparatus defined in claim 5 further comprising:
   nozzle means located in said end of said first linkage where said sensing means is located, for emitting a stream of water that extends between said sensing means and said target; wherein
   said sensing means is comprised of an acoustic transducer; and
   said sensing signal, said first echo and said second echo are comprised of ultrasonic waves; whereby
   said sensing signal travels from said sensing means to said test object through the medium of water, and said first echo and said second echo travel between said test object and said sensing means through the medium of water.

7. The ultrasonic testing apparatus defined in claim 3 further comprising:
   a second linkage located on the opposite side of said test object from said first linkage;
   receiving means located at one end of said second linkage for receiving said sensing signals; and
   second adjusting means for adjusting said second linkage responsive to the orientation of said sensing means.

8. The ultrasonic testing apparatus defined in claim 7 wherein:
   said receiving means receives said sensing signals and produces output signals corresponding to the maximum amplitudes of said sensing signals received by said receiving means; and
   said angle of incidence deviates no more than 10° from normality.

9. The ultrasonic testing apparatus defined in claim 8 further comprising:
   signal attenuation measurement means for generating attenuation signals corresponding to the measured differences between said maximum amplitudes of said output signals and the theoretical maximum amplitudes said output signals would have if said sensing signals traveled through said test object without encountering any subsurface irregularities; whereby
   the presence of irregularities in the subsurface structure of said test object can be detected.

10. The ultrasonic testing apparatus defined in claim 9 further comprising:
    collating means for collating said attenuation signals with said targets to form data points; and
    dispaly means for displaying said data points, 11. The ultrasonic testing apparatus defined in claim 10 further comprising:
    first nozzle means located in said end of said first linkage where said sensing means is located, for emitting a stream of water that extends between said sensing means and said targets, respectively;
    second nozzle means located in said end of said second linkage where said receiving means is located, for emitting a stream of water that extends between said receiving means and said test object; wherein
    said sensing means and said receiving means are each comprised of an acoustic transducer; and
    said sensing signals are ultrasonic waves; whereby
    said ultrasonic waves travel from said sensing means to said targets, respectively, and after passing through said test object, to said receiving means through the medium of water.

12. The ultrasonic testing apparatus defined in claim 11 wherein:
    said members of said second linkage respectively rotate about parallel lateral axes;
    said second adjusting means includes roll means for rotating said second linkage about a longitudinal axis lying perpendicular to said parallel lateral axes of said second linkage; and
    said translation means translationally moves said second linkage so that said longitudinal axis of said second linkage remains colinear with said longitudinal axis of said first linkage.

13. The ultrasonic testing apparatus defined in claim 7 wherein:
    said sensing means is a first acoustic transducer; and
    said receiving means is a second acoustic transducer.

14. The ultrasonic testing apparatus defined in claim 13 wherein:
    said angle of incidence deviates no more than 10° from normality; and
    said second adjusting means adjusts said second linkage so that said second acoustic transducer receives said ultrasonic waves emitted by said first acoustic transducer.

15. The ultrasonic testing apparatus defined in claim 1 wherein:
    said first linkage is capable of moving said sensing means in a pitch plane while maintaining the same point of incidence of said sensing signals on said test object;
    pitch means for moving said sensing means in said pitch plane; and
    roll means for rolling said first linkage about an axis lying in said pitch plane.

16. The ultrasonic testing apparatus defined in claim 1 wherein:
    said sensing means is an acoustic transducer.

17. The ultrasonic testing apparatus defined in claim 16 wherein
    said desired angle of incidence is approximately normal.

* * * * *